United States Patent [19]
Hill, III et al.

[11] Patent Number: 5,499,632
[45] Date of Patent: Mar. 19, 1996

[54] GUIDE WIRE MIGRATION CONTROLLER

[75] Inventors: E. Richard Hill, III, Berkely; Glenn Davis, Sunnyvale; Brian Farley, Los Altos, all of Calif.

[73] Assignee: Devices for Vascular Intervention, Redwood City, Calif.

[21] Appl. No.: 237,690

[22] Filed: May 4, 1994

[51] Int. Cl.$^6$ .................................................. A61M 37/00
[52] U.S. Cl. ............................ 128/772; 128/657; 604/95
[58] Field of Search .................................. 606/159, 167, 606/168, 169, 170, 171, 172, 180, 184, 185; 128/772

[56]  References Cited

U.S. PATENT DOCUMENTS

| | | | |
|---|---|---|---|
| Re. 33,569 | 4/1991 | Gifford, III | 606/159 |
| 4,732,163 | 3/1988 | Bonello et al. | 128/772 |
| 4,771,774 | 9/1988 | Simpson | 128/305 |
| 4,781,186 | 11/1988 | Simpson | 128/305 |
| 4,794,931 | 1/1989 | Yock | 128/660 |
| 4,798,598 | 1/1989 | Bonello et al. | 128/772 X |
| 4,979,951 | 12/1990 | Simpson | 606/159 |
| 4,986,807 | 1/1991 | Farr | 606/159 X |
| 5,000,185 | 3/1991 | Yock | 128/662 |
| 5,007,917 | 4/1991 | Evans | 606/170 |
| 5,041,089 | 8/1991 | Mueller et al. | 604/96 |
| 5,071,425 | 12/1991 | Gifford, III | 606/159 |
| 5,078,722 | 1/1992 | Stevens | 606/159 |
| 5,084,010 | 1/1992 | Plaia | 604/22 |
| 5,085,662 | 2/1992 | Willard | 606/159 |
| 5,087,265 | 2/1992 | Summers | 606/159 |
| 5,092,873 | 3/1992 | Simpson et al. | 606/159 |
| 5,100,424 | 3/1992 | Jung | 606/159 |
| 5,108,411 | 4/1992 | McKenzie | 606/159 |
| 5,135,531 | 8/1992 | Shiber | 606/159 |
| 5,156,610 | 10/1992 | Reger | 606/159 |
| 5,158,564 | 10/1992 | Schnepp-Pesch | 606/159 |
| 5,226,909 | 7/1993 | Evans | 606/159 |
| 5,250,059 | 10/1993 | Andreas | 606/159 |
| 5,312,338 | 5/1994 | Nelson et al. | 128/772 X |

Primary Examiner—Sam Rimell
Attorney, Agent, or Firm—Douglas A. Chaikin

[57] ABSTRACT

Disclosed herein is a guide wire migration controller device. The device includes a housing, a gripper insertable in the housing and a locking member for keeping the gripper within the housing. The gripper grips a guide wire operated by a motor drive unit. The gripper limits the migrational movement of the guide wire by gripping the guide wire and limiting the movement to the amount of tolerance between the gripper and the housing and locking member. The gripper rotates freely within the housing depending upon the rotational movement of the catheter torque cable wire. In a preferred embodiment the migrational movement of the guide wire along its longitudinal axis is translated into slidable movement of the controller relative to the motor drive unit.

17 Claims, 3 Drawing Sheets

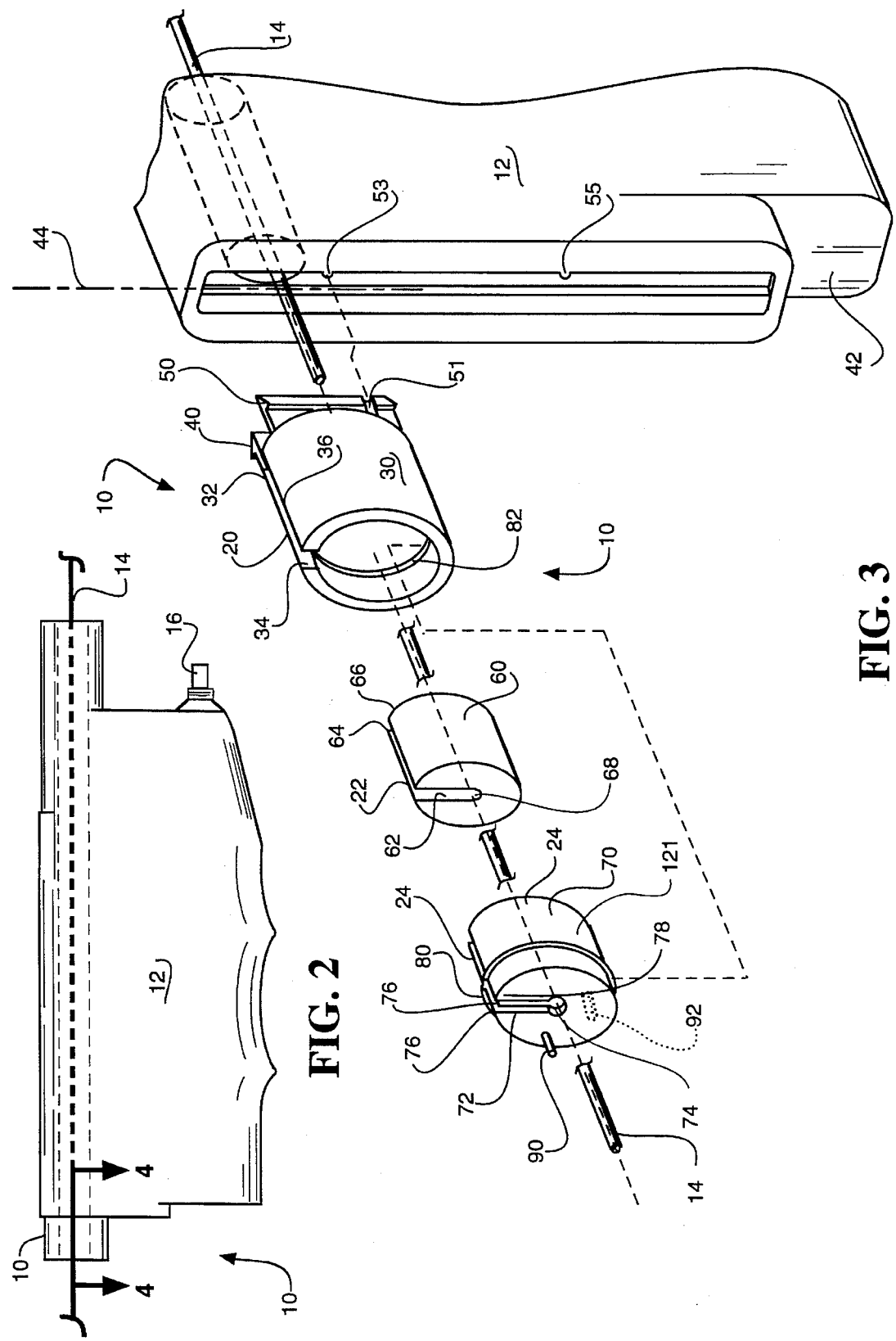

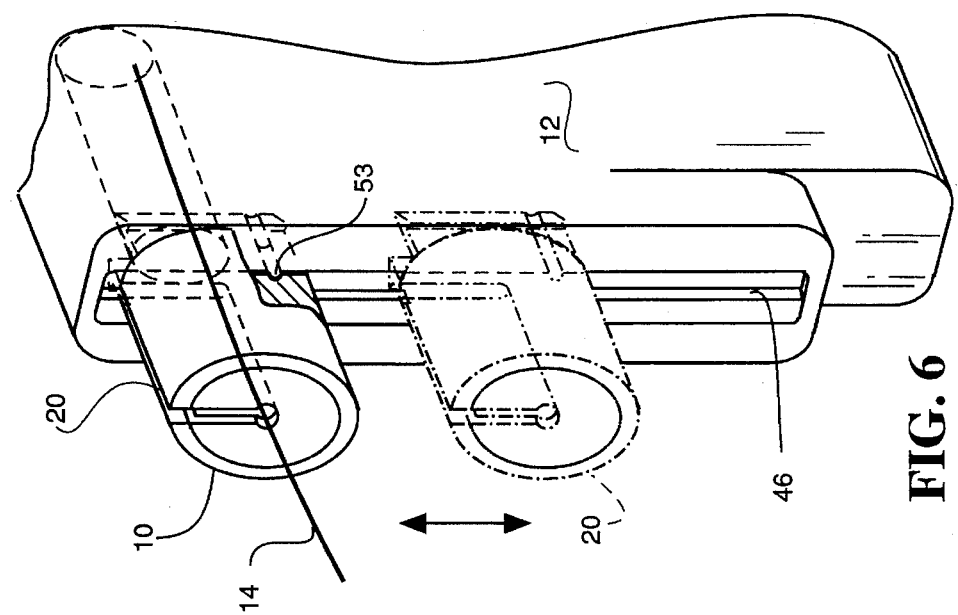
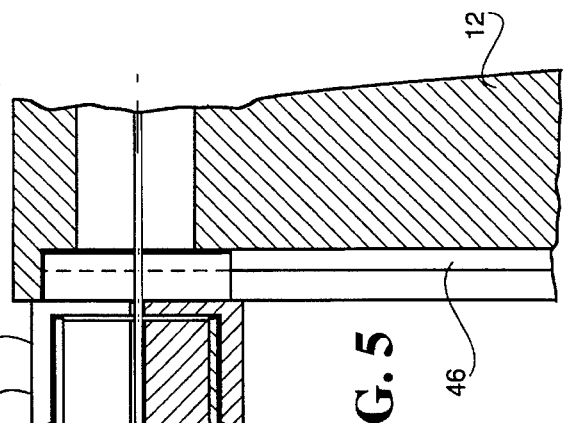
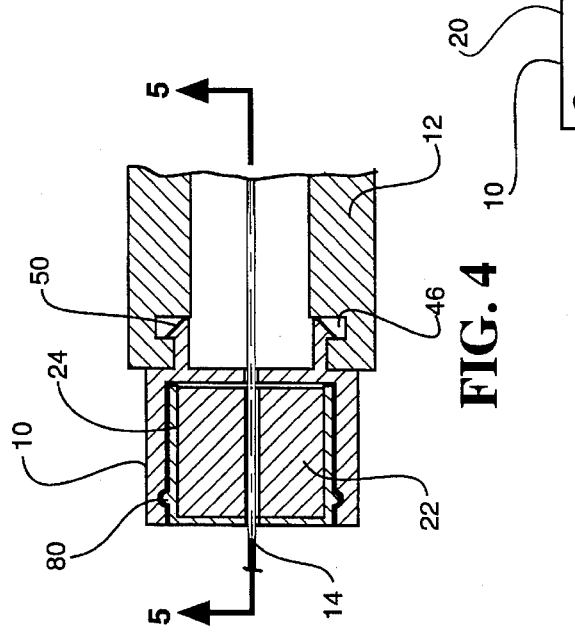
FIG. 6
FIG. 5
FIG. 4

GUIDE WIRE MIGRATION CONTROLLER

BACKGROUND OF THE INVENTION

1. Field of Invention

This invention relates to catheter devices using guide wires for guiding the catheter to the desired location within a body. More particularly, this invention relates to such catheter devices which include motor driven drive unit for driving a torque cable. Specifically, the invention herein relates to structures which control such a guide wire from migrating along its longitudinal axis while the torque cable is being operated by a motor drive unit.

2. Previous Art:

As described in U.S. Pat. Nos. 5,250,059; 5,084,010 and 4,479,952 which are specifically incorporated herein by reference, there exists a plethora of different catheter designs. In many catheter designs, specifically where directional atherectomy catheters are used, it is desirable to use a guide wire to guide the catheter to the desired position within a body.

In order to guide the catheter to the desired position within the body, the catheter is used in conjunction with a motor drive unit, a torque cable and a guide wire. Typically, the torque cable consists of a cable having a hollow interior wherein one end of the cable is connected to the motor drive unit and the other end of the unit is connected to a work element. Work elements can include cutting devices, ablation elements or even telemetry. The guide wire is located in the central interior opening of the torque cable. The guide wire is made from material such as spring steel or Nitinol. The guide wire typically has a diameter of between 0.009" and 0.0018".

Typically, the guide wire is manipulated to the desired location by rotating and hand feeding the guide wire through the cutter torque cable via a conduit inside the motor drive unit. Unfortunately, when the cutter torque cable is spun by the motor drive unit, the spinning action of the cutter torque cable against the guide wire causes a sympathetic spinning action of the guide wire, which is located in and protrudes from the central lumen in the cutter torque cable. The cutter torque cable can also be translated along the longitudinal axis of cable with or without the rotation of the cutter. This translational movement of the cutter torque cable also causes sympathetic translation of the guide wire which is located in and protrudes from the central lumen of the cutter torque cable. Such migration of the guide wire can cause trauma to the biological conduit near the treatment site. While controlling the axial migration of the guide wire, the guide wire needs to rotate freely as the sympathetic action between the cutter torque cable and guide wire may varyingly dictate. If the guide wire is kept from rotating at the proximal end, the spinning action of the cutter torque cable against the guide wire may cause the distal end of the guide wire to wind up and fail.

What is needed is a device for controlling the migration of the guide wire while allowing the guide wire to spin during rotation and longitudinal motion of the cutter torque cable. The device for controlling the guide wire migration should fit within the conventional motor drive system and should not add greatly to the expense of the operation.

SUMMARY OF THE INVENTION

It is a general object of this invention to provide a guide wire migration controller which prevents substantial migration of the guide wire during catheter cutting operation.

It is another object of this invention to provide a device for controlling migration of the guide wire during operation of the catheter cutting which adapts easily with the conventional motor drive unit.

It is another object of this invention to provide a guide wire migration controller which prevents substantial migration of the guide wire without interfering with rotation of the torque cable.

In accordance with the above objects and those that will become apparent below, a guide wire migration controller is provided in accordance with this invention which comprises:

a controller including:
- a housing connectable to the motor drive;
- a guide wire gripper for gripping the guide wire along its longitudinal axis and being insertable within the housing; and
- a locking member for locking the guide wire gripper within the housing, whereby, the gripper is locked within the housing preventing guide wire migration along the longitudinal axis.

In a preferred embodiment, the motor drive unit has a distal side having a track member with a track axis approximately 90° to the longitudinal axis of the guide wire and the housing has a rail member for connection to the motor drive unit track member. The rail member is slidably connectable to the track member and slidable along the track axis.

In a preferred embodiment, the gripper comprises a solid body having a keyhole opening. The gripper is made from a polymeric material which creates a friction grip with the guide wire. As will be appreciated, the guide wire is able to rotate within the housing with the gripper attached therein; however, it is limited from movement along the longitudinal axis by the space between the gripper and the housing.

In another preferred embodiment, each of the gripper housing and locking member define a solid body having a central keyhole opening, which is normally outwardly extending, but upon appropriate force may have its opposed open ends brought together.

In another preferred embodiment, the locking member has a raised annulus which slidably and rotatably fits within an inner race in the housing for releasable and locking connection therewith. In this preferred embodiment, the gripper and the locking member rotate freely with the rotational movement of the guide wire.

It is an advantage of the guide wire migration controller in accordance with this invention to provide a device which can be readily adapted to conventional motor drive units, catheters and guide wires.

BRIEF DESCRIPTION OF THE DRAWING

For a further understanding of the objects and advantages of the present invention, reference should be had to the following detailed description, taken in conjunction with the accompanying drawing, in which like parts are given like reference numerals and wherein:

FIG. 2 illustrates the guide wire migration controller in accordance with this invention in conjunction with a motor driven catheter assembly.

FIG. 3 is an exploded view of the guide wire migration controller of FIG. 2 connectable to a motor drive unit.

FIG. 4 is a cross-sectional view of the guide wire migration controller of FIG. 2 taken along line 4—4 and looking in the direction of the arrows.

FIG. 5 is a cross-sectional view of the guide wire migration controller of FIG. 4 taken along line 5—5 and looking in the direction of the arrows.

FIG. 6 is a perspective view of the guide wire migration controller in accordance with this invention in use.

DETAILED DESCRIPTION OF THE INVENTION

Figure 1:
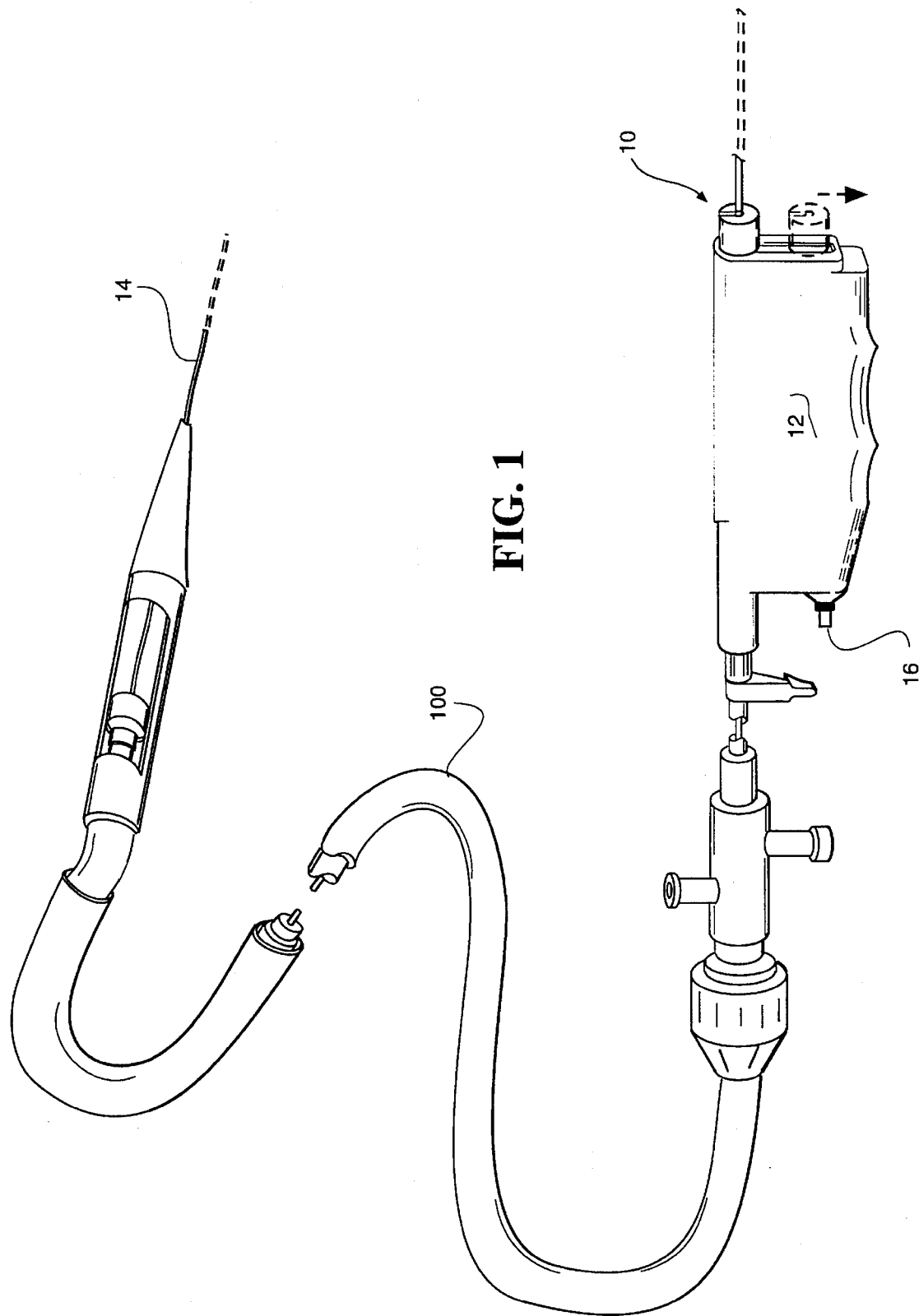
FIG. 1 illustrates, in perspective view, the guide wire migration controller in accordance with this invention in connection with a typical catheter.

The invention will now be described with respect to FIG. 1 which illustrates the guide wire migration controller generally denoted by the reference numeral 10 in use with a catheter 100. As is conventional, the guide wire 14 is fed though a lumen in the torque cable to the desired position. Once at the desired position, the torque cable is rotated. Using the guide wire migration controller 10, the guide wire 14 remains substantially in place despite the activation of the motor drive unit 12 and consequently the torque cable.

With particular reference to FIG. 2 there is seen the guide wire migration controller (controller) 10 in accordance with this invention in conjunction with a motor driven catheter assembly. The guide wire migration controller 10 illustrated in FIG. 1 is connected to a motor drive unit 12. A guide wire 14 allows a catheter 100 (FIG. 1) to follow and be guided thereby.

The torque cable is rotated by motor drive unit 12 by operating a switch 16. The switch 16 typically toggles the operation of the motor drive unit 12 in an on/off condition.

With respect to FIG. 3, there is shown an exploded enlarged view of the guide wire migration controller 10. The guide wire migration controller 10 includes a housing 20, a gripper 22 insertable within the housing and a locking member 24 for locking the gripper into the housing 20.

The housing 20 includes a body 30. The body 30 defines a split ring having a longitudinal opening 32. The opening allows the body to be squeezed so that opening ends 34 and 36 may be moved toward each other. As will be appreciated, it is preferred that the body be made of a plastic material so that when the ends are released the body is normally urged to the open position wherein the longitudinal opening 32 is again seen. It will be appreciated that the preferred embodiment utilizes the opening for removable connection with the motor drive unit 12.

The housing 20 includes a set of projecting ears 40. The ears 40 project and extend from the body 30. The motor drive unit 12 has a distal end which is adjacent the operating end of the guide wire 14, and a proximal end 42 which is opposite the distal end. The proximal end of 42 of the motor drive 12 has a track axis 44. A track member 46 is provided within the proximal end 42 along the track axis 44.

The ears 40 define rail members 50. The rail members 50 are sized and shaped for compatible connection with the track member 46. The ends 34 and 36 and the housing 20 are squeezed together forcing normally outwardly urging ends 34 and 36 together so that the rail members 50 may be connected to the track member 46 for slidable engagement. The slidable movement is in the direction of the track axis 44.

The guide wire migration controller includes the gripper 22 as set forth above. The gripper 22 has a body 60 having an opening 62. The opening 62 comprises a slice removed from the gripper 22. The slice can be from several thousandths of an inch to one hundredth of an inch. As with the housing body 30, the gripper body 60 has ends 64 and 66 which are normally in the open position, with the ends 64 and 66 urged apart. The slice terminates at a radius end 68. The radius end 68 is sized and shaped for compatible gripping of the guide wire 14.

The gripper 22 is made from a polymeric material suitable for gripping a thin metal wire. Such polymers include polyurethanes, RTV silicone, silicone rubbers and elastomeric materials in general. Also, it is preferred that the gripper 22 be made of a plastic material which will keep the ends 64 and 66 in a normally openly urged position. Thus, the opening 62 will be easily identifiable under normal circumstances. It will be appreciated that when the gripper is inserted within the housing 20, the ends 64 and 66 are moved together providing additional gripping force on the guide wire in the opening 62.

The guide wire migration controller 10 additionally includes a locking member 24 for locking the gripper 22 within the housing 20. The locking member 24 has a body 70 also having a keyhole opening 72. The keyhole opening 72 has a center opening 74 and opposed ends 76 and 78. As described earlier with reference to the body 30 and body 60 of the housing and gripper respectively, the opposed ends 76 and 78 are normally urged apart for similar reasons. The guide wire 14 fits within center opening 74 and operates similarly to that discussed above with reference to the gripper 22. The body 70 includes an annulus 80 in the preferred embodiment. In the preferred embodiment, the housing body 30 includes an inner race 82. The inner race 82 and the annulus 80 are sized and shaped for compatible rotatable matable connection. As will be appreciated once the guide wire 14 is gripped by the gripper 22 and locked within the housing 20, it should be provided with a means for rotating. The combination of the annulus 80 and inner race 92 allows for such rotation. Thus, the guide wire 14 may rotate freely while the gripper 22 grips the guide wire 14 and rotates together with the locking member 24 through the combination of the inner race 82 and annulus 80.

As illustrated with reference to FIG. 4 the guide wire migration controller 10 is connected to the motor drive unit 12. The rail members 50 fit snug within the track member 46. The gripper 22 is held in place by the locking member 24. The guide wire 14 is securely held by the gripper 22. As the guide wire is sympathetically rotated by the motor drive 12, the guide wire rotates with the gripper 22 attached. The locking member 24 rotates with the gripper with the annulus 20 rotating within the race 82. It will be appreciated with respect to FIG. 3 that the longitudinal opening 32 in the housing 20, the keyhole opening 72 in the locking member 24, and the guide wire gripper opening 62 align to receive the guide wire and to permit removal of the guide wire.

With respect to FIG. 5 there is shown a side elevational cross-sectional view of the guide wire migration controller 10. As illustrated in FIGS. 5 and 6, the guide wire migration controller is able to slide within the track member 46 from one position to another along the track axis 44.

With respect to FIGS. 3, 5 and 6, there is shown the guide wire migration controller in use. As seen, with particular reference to FIG. 6, the guide wire 14 is hand fed through the motor drive unit 12 into the catheter. During the hand feeding process, the housing 20 is moved away from the entrance of the catheter where the guide wire 14 is fed. This is accomplished by moving the catheter along its track 46 to a second position, generally shown in phantom in FIG. 6.

The rail member has a detent cutout 51 on one of its sides which is compatible with a protuberance 53 on the track member 46. A second protuberance 55 also extends into track member 46 as illustrated clearly in FIG. 5.

In the first position, the detent cutout 51 is secured at position 1 by protuberance 53. In the second position where the housing 20 is moved away from the entrance of the catheter, the detent cutout 51 is moved to a second position wherein the detent cutout 51 is secured at the second position by protuberance 55.

In order relocate and secure the guide wire 14 to the migration controller 10, the openings in each of the locking member 24, the gripper 22 and the housing 20 are aligned for compatible connection with the guide wire 14. In order to facilitate this, the locking member 24 is provided with a locating member 90.

As will be appreciated, since the gripper 22 is normally outwardly extending and diverging from its ends 64 and 66, it does not rotate freely within the housing 20 or locking member 24. Thus, the opening 62 and opening 74 of each of the gripper 22 and the locking member 24 are aligned and generally stay in alignment. The locating member 90 is used to align the openings 62 and 74 of the gripper 22 and locking member 24, respectively, with the opening 32 of the housing 20.

In the second position, the slots are aligned prior to moving to the first position for capturing the guide wire. Thus, the physician has little or no trouble in moving the guide wire migration controller 10 from the first to second position or from the second to first positions.

In an alternate embodiment as shown in phantom in FIG. 3, the locating member comprises a ridge 92 used for the same purpose as locating member 90.

While the foregoing detailed description has described details of the guide wire migration controller in accordance with this invention, it is to be understood that the above description is illustrative only and not limiting of the disclosed invention. Particularly, the types of opening and materials used may be varied within the scope and spirit of this invention. Additionally, various types of motor drive units, as well as guide wires, may be utilized, again within the scope and spirit of this invention. It will be appreciated that this invention is to be limited only by the claims as set forth below.

What is claimed is:

1. A guide wire migration controller for use with a motor driven unit and a guide wire, the guide wire having a longitudinal axis and the guide wire migration controller controlling migration of the guide wire along the longitudinal axis, the guide wire migration controller comprising:

a motor drive unit;

a housing connectable to the motor drive unit;

a guide wire gripper for gripping the guide wire along its longitudinal axis and being insertable within the housing; and a locking member for locking the guide wire gripper within the housing, whereby, the gripper is locked within the housing controlling guide wire migration along the longitudinal axis.

2. A guide wire migration controller as set forth in claim 1, wherein, the housing and the gripper define a space therebetween, once the gripper is locked within the housing, the guide wire motion along the longitudinal axis is limited by the space between the gripper and the housing.

3. A guide wire migration controller as set forth in claim 1, wherein the motor drive has a distal end and a proximal end opposite therefrom, and wherein the motor drive unit has a track member having a track axis along its distal end, the distal end having an axis approximately 90° to the longitudinal axis of the guide wire and wherein the housing has a rail member for connection with the motor drive track member, the rail member being slidably connectable to the track member and the track axis defining the direction of motion between the housing and the motor drive, whereby migration of the guide wire along its longitudinal axis is translated to slidable movement by the housing along the track axis.

4. A guide wire migration controller as set forth in claim 1, wherein the guide wire gripper defines a friction grip.

5. A guide wire migration controller as set forth in claim 4, wherein the gripper defines a solid body having a central opening extending through the central portion of the body along the longitudinal axis defined by the guide wire the gripper firmly gripping the guide wire while permitting rotation of the guide wire within the housing.

6. A guide wire migration controller as set forth in claim 5, wherein the gripper is made from polyymeric material suitable for gripping thin metal wire.

7. A guide wire migration controller as set forth in claim 5, wherein the gripper is made from rubber.

8. A guide wire migration controller as set forth in claim 1 wherein the locking member defines a solid body having a central keyhole opening through the body and generally along the longitudinal axis defined by the guide wire.

9. A guide wire migration controller as set forth in claim 3, wherein the housing has an inner race detent and wherein the locking member has an outer annular projection extending from the body for compatible slidable and locking mating with the inner race detent of the housing.

10. A guide wire migration controller as set forth in claim 9, wherein the housing has a central opening and wherein the housing has ears to define rail members for suitable connection with the motor drive unit.

11. A guide wire migration controller for use with a motor drive unit, the guide wire having a longitudinal axis and the controller controlling migration along the longitudinal axis, the guide wire migration controller comprising:

a motor drive unit;

a housing connectable to the motor drive unit;

a locking member being insertable within the housing; and a guide wire gripper being insertable within the locking member for gripping the guide wire along its longitudinal axis and the locking member locking the guide wire gripper within the housing, whereby the gripper is locked within the housing preventing the guide wire migration along the longitudinal axis.

12. A guide wire migration controller as set forth in claim 11, wherein the locking member is sized and shaped to prevent rotation of the gripper within the locking member.

13. A guide wire migration controller as set forth in claim 11, wherein the guide wire gripper is sized and shaped for preventing rotation of the guide wire gripper within the locking member.

14. A guide wire migration controller as set forth in claim 3, wherein the housing rail member has a cutout detente and wherein the motor drive unit has a first protuberance in a first position extending into the track axis and a second protuberance in a second position extending into the track axis, and wherein in the first position the guide wire migration controller is aligned with an opening in the motor drive unit adapted for a catheter and in the second position is moved away from the opening.

15. A guide wire migration controller as set forth in claim 14, wherein the locking member includes an exterior surface having a locating member for aligning the locking member, gripper and housing for capturing the guide wire.

16. A guide wire migration controller as set forth in claim 11 wherein said housing includes a longitudinal opening, said locking member includes a keyhole opening and said guide wire gripper includes an opening; wherein said longitudinal opening, said keyhole opening and said guide wire opening align to receive said guide wire and to permit removal of said guide wire.

17. A guidewire migration controller for controlling guidewire migration, comprising:

a motor drive unit;

a housing connected to the motor drive unit;

a guidewire gripper for gripping the guidewire, the guidewire gripper being insertable within the housing; and a locking member for locking the guidewire gripper within the housing, whereby, the gripper locks within the housing to control guidewire migration.

* * * * *